United States Patent
Kanj et al.

(10) Patent No.: US 10,845,291 B2
(45) Date of Patent: Nov. 24, 2020

(54) RADIAL CORE FLOODING APPARATUS AND METHOD FOR ANALYSIS OF STATIC AND/OR DYNAMIC PROPERTIES OF RESERVOIR ROCK

(71) Applicant: King Fahd University of Petroleum and Minerals, Dhahran (SA)

(72) Inventors: Mazen Yousef Kanj, Dhahran (SA); Xianmin Zhou, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 78 days.

(21) Appl. No.: 15/980,304

(22) Filed: May 15, 2018

(65) Prior Publication Data

US 2018/0335374 A1 Nov. 22, 2018

Related U.S. Application Data

(60) Provisional application No. 62/506,830, filed on May 16, 2017.

(51) Int. Cl.
| | |
|---|---|
| *G01N 15/08* | (2006.01) |
| *E21B 49/02* | (2006.01) |
| *E21B 49/00* | (2006.01) |
| *G01N 33/24* | (2006.01) |
| *E21B 49/08* | (2006.01) |

(52) U.S. Cl.
CPC ....... *G01N 15/0826* (2013.01); *E21B 49/006* (2013.01); *E21B 49/02* (2013.01); *G01N 15/0806* (2013.01); *G01N 33/241* (2013.01); *E21B 2049/085* (2013.01)

(58) Field of Classification Search
CPC .......... G01N 15/0826; G01N 15/0806; G01N 15/08–0893; G01N 2015/0813–0873
USPC .................... 73/38, 152.07, 152.11
See application file for complete search history.

(56) References Cited

U.S. PATENT DOCUMENTS

| | | | | | |
|---|---|---|---|---|---|
| 2,157,135 | A | * | 5/1939 | Little | G01N 15/0826 73/38 |
| 2,465,948 | A | * | 3/1949 | Weige | G01N 15/08 73/38 |
| 2,498,198 | A | * | 2/1950 | Beeson | G01N 15/0826 73/38 |

(Continued)

FOREIGN PATENT DOCUMENTS

| | | |
|---|---|---|
| CN | 2613754 Y | 4/2004 |
| CN | 103926180 A | 7/2014 |
| FR | 2 734 364 | 11/1996 |

*Primary Examiner* — Alexander A Mercado
(74) *Attorney, Agent, or Firm* — Oblon, McClelland, Maier & Neustadt, L.L.P.

(57) ABSTRACT

Apparatuses and methods suitable for (i) measuring lithological or petro-physical properties of reservoir core sample including shale rock; (ii) evaluating the degree of formation damage caused by foreign fluid into formation; (iii) conducting dynamic experiments, such as water flooding, chemical solution flooding, and supercritical $CO_2$ injection to displacing oil tests; (iv) simulating physical radial flow experiments using reservoir core sample(s) at conditions of temperature up to 150° C. and pressure up to 6000 psi, are provided involving radial flow through the core sample(s) having at least partially hollow centers in an axial direction, up to annular axial cross-sections.

20 Claims, 8 Drawing Sheets

(56) References Cited

U.S. PATENT DOCUMENTS

| | | | | |
|---|---|---|---|---|
| 2,539,355 A * | 1/1951 | Reichertz | G01N 15/08 | 73/38 |
| 2,612,036 A * | 9/1952 | Angona | G01N 33/246 | 73/38 |
| 2,641,922 A * | 6/1953 | Smith | G01N 27/16 | 73/19.05 |
| 2,705,418 A * | 4/1955 | Francis | G01N 15/0826 | 73/38 |
| 2,724,963 A * | 11/1955 | Ten Brink | G01N 15/0826 | 73/38 |
| 2,821,680 A * | 1/1958 | Slusser | G01N 15/0806 | 324/376 |
| 2,842,958 A * | 7/1958 | Roark | G01N 15/0806 | 73/38 |
| 2,913,658 A * | 11/1959 | Burdine | G01R 33/30 | 324/318 |
| 3,018,660 A * | 1/1962 | Schmid | G01N 33/24 | 73/152.09 |
| 3,023,606 A * | 3/1962 | Sarem | G01N 15/082 | 73/38 |
| 3,066,524 A * | 12/1962 | Overhuls | G01N 15/0806 | 73/38 |
| 3,289,467 A * | 12/1966 | Parker | G01N 33/00 | 73/61.63 |
| 3,636,751 A * | 1/1972 | Pasini, III | G01N 15/082 | 73/38 |
| 3,839,899 A * | 10/1974 | McMillen | G01B 13/02 | 73/38 |
| 4,478,069 A * | 10/1984 | Zuckerwar | E21B 47/10 | 73/152.18 |
| 4,524,604 A * | 6/1985 | Vondran | G01N 15/0806 | 249/183 |
| 4,552,011 A * | 11/1985 | Wiley | G01N 15/0826 | 73/1.64 |
| 4,555,934 A * | 12/1985 | Freeman | G01N 15/0826 | 73/38 |
| 4,561,289 A * | 12/1985 | Jones | G01N 15/0806 | 73/38 |
| 4,573,342 A * | 3/1986 | Jones | G01N 15/08 | 73/38 |
| 4,599,891 A * | 7/1986 | Brauer | G01N 15/0806 | 73/38 |
| 4,643,019 A * | 2/1987 | Jones | G01N 15/0806 | 73/38 |
| 4,649,737 A * | 3/1987 | Jones | G01N 15/08 | 73/38 |
| 4,679,421 A * | 7/1987 | Barree | G01N 33/241 | 73/38 |
| 4,688,238 A * | 8/1987 | Sprunt | G01N 23/046 | 378/210 |
| 4,710,948 A * | 12/1987 | Withjack | G01N 23/04 | 378/208 |
| 4,753,107 A * | 6/1988 | Reed | G01N 15/0806 | 73/38 |
| 4,799,382 A * | 1/1989 | Sprunt | G01N 15/088 | 378/4 |
| 4,864,846 A * | 9/1989 | Jones | G01N 15/0806 | 73/38 |
| 5,025,668 A | 6/1991 | Sarda et al. | | |
| 5,065,421 A * | 11/1991 | Morineau | G01N 33/241 | 378/208 |
| 5,167,139 A * | 12/1992 | Lafargue | G01N 33/241 | 73/38 |
| 5,226,310 A * | 7/1993 | Steiger | E21B 49/006 | 73/38 |
| 5,263,360 A * | 11/1993 | Blauch | C09K 8/58 | 166/250.02 |
| 5,269,999 A * | 12/1993 | Smesny | B29C 43/18 | 264/112 |
| 5,363,692 A * | 11/1994 | Lafargue | G01N 33/241 | 73/38 |
| 5,379,645 A * | 1/1995 | Smart | G01N 3/10 | 73/794 |
| 5,563,333 A * | 10/1996 | Haines | G01N 15/0806 | 73/38 |
| 5,698,772 A * | 12/1997 | Deruyter | G01N 15/0826 | 73/38 |
| 5,868,030 A * | 2/1999 | Brumley | G01B 5/30 | 73/784 |
| 5,979,223 A * | 11/1999 | Fleury | G01N 33/241 | 73/38 |
| 6,269,684 B1 * | 8/2001 | Maki, Jr. | E21B 49/005 | 73/53.01 |
| 9,108,138 B2 * | 8/2015 | Hao | B01D 46/2411 | |
| 9,464,523 B1 * | 10/2016 | Grove | E21B 49/088 | |
| 9,903,826 B2 * | 2/2018 | Alshehri | G01N 23/046 | |
| 2004/0053327 A1 | 3/2004 | Muller | G01N 21/6452 | 435/7.1 |
| 2008/0083266 A1 * | 4/2008 | Gupta | G01N 15/08 | 73/38 |
| 2008/0110243 A1 * | 5/2008 | Burke | B01D 65/102 | 73/38 |
| 2012/0118041 A1 * | 5/2012 | He | G01N 7/14 | 73/23.35 |
| 2013/0276554 A1 * | 10/2013 | Matthews | E21B 25/005 | 73/864 |
| 2015/0059447 A1 * | 3/2015 | Rickards | G01N 19/00 | 73/61.41 |
| 2015/0135815 A1 * | 5/2015 | Blue | G01N 15/0806 | 73/152.18 |
| 2018/0364142 A1 * | 12/2018 | Georgi | G01N 15/0826 | |
| 2019/0011422 A1 * | 1/2019 | McGregor | E21B 49/088 | |
| 2019/0025169 A1 * | 1/2019 | Zhang | G01N 3/18 | |
| 2019/0187039 A1 * | 6/2019 | Su | G01N 15/082 | |
| 2019/0339183 A1 * | 11/2019 | Roberts | G01N 3/36 | |
| 2019/0383786 A1 * | 12/2019 | Hugghins | G01N 3/18 | |

* cited by examiner

RADIAL CORE FLOODING APPARATUS AND METHOD FOR ANALYSIS OF STATIC AND/OR DYNAMIC PROPERTIES OF RESERVOIR ROCK

CROSS-REFERENCE TO RELATED APPLICATIONS

This application claims priority to U.S. provisional application Ser. No. 62/506,830, filed May 16, 2017, which is incorporated by reference herein in its entirety.

BACKGROUND OF THE INVENTION

Field of the Invention

The present invention relates to an apparatus and method for determining different physical parameters of reservoir core samples and evaluating performance in enhanced oil recovery (EOR) and improved oil recovery (IOR), for example when fluid injection and production occurs in the pattern of radial flow at evaluated conditions.

Description of the Related Art

In recovering oil and natural gas from a subterranean reservoir, such as a sandstone, shale, and/or carbonate reservoir, certain lithological or petro-physical properties, generally static properties, and well formation damage of the reservoir rock are routinely analyzed and determined in laboratory. A variety of dynamic displacement experiments exist, such as oil displaced by water, chemical solutions, and/or supercritical $CO_2$ injection. These experiments are used in order to determine properties of the reservoir rock and use the resulting information to improve and/or maximize oil and gas recovery from the reservoir.

Linear, one-dimensional (1D), and axial displacement experiments are used widely in reservoir engineering analytics. When issues occur at or near the wellbore, such as wellbore damage, decline of injection capacity, and/or decline of production capacity, experiments physically simulating these problems using linear, 1D, and axial displacement pattern(s) have not been entirely satisfactory due to their failure to capture and/or evaluate radial flow in lithological formation(s) at and/or near the wellbore.

Radial flow usually occurs around the base hole(s), inlet (s), and/or outlet(s) of the injector and the producer. The lithological formations near the wellbore can be damaged by a variety of mechanisms, including fines migration caused by the interaction between injection agent(s) and the rock matrix, paraffin deposition, and/or asphalting deposition, which can result in formation damage. Moreover damage mechanisms can change characteristics of the near-wellbore formation, as well as the flow profiles of the injector and producer. Such damage can contribute to poor displacement efficiency, diminution, and/or loss of oil production.

FR 2 734 364 A1 discloses a cell, useful for measuring petro-physical and poromechanical characteristics of a rock sample, having a body containing a measuring chamber, a heater for the measuring chamber, bearings to receive the sample, means to apply an axial constraint to the sample via the bearings, a sleeve sealing around the sample, bearings to isolate the sample from the measuring chamber, means of applying a hydraulic pressure in the measuring chamber to generate radial constraints on the sample through the sleeve. FR 2 734 364 A1 thus provides a cell or core holder to measure rock characteristics, electrical resistance of cylindrical core sample during drilling process. The cell is a typical hydraulic core holder that applies to some research topics in the drilling industry. Two pumps, a radial pump and axial pump, were used to seal a core sample into a rubber sleeve. A radial pump provides radial force for confining pressure to its core sample, and then an axial pump provides a support force to core sample. However, FR 2 734 364 A1 is used to conduct one-dimensional experiments in terms of injecting test fluid from one end to core sample, and then out the other end, and does not disclose application to a core sample having an at least partially hollow core. FR 2 734 364 A1 does not disclose three-dimensional experiments.

CN 103926180 A discloses a flexible core axial stress loading method in pore fluid displacement tests, involving arranging a tested core in a sealing rubber cover; arranging the rubber cover in a closed space; arranging the closed space in a constant-temperature environment capable of being metered; applying same axial pressures with measurable flexibility on a coated core in the upper and lower vertical axis directions by an elastic mechanical pressure applying method; uniformly applying surround pressures capable of being metered on surfaces, in the other directions, of the coated tested core in a manner of injecting gas or liquid into the closed space; injecting gas or liquid capable of being metered in the sealing rubber cover from the lower vertical axis direction of the tested core; discharging gas or liquid capable of being metered from the external closed space from the upper vertical axis direction of the tested core; and collecting sound wave signals of ends of the upper and lower vertical axis directions of the tested core by sound wave probes. CN 103926180 A thus describes a core holder and a flexible core axial stress loading method to prevent crushing test core samples during displacement experiments. A core holder is applied to a cylindrical core sample for displacing experiment, and sound wave probes mounted the upper end plug and lower end plug of core sample receive sound signals. A test cylindrical core sample cannot be crushed according to the received sound wave signals, so its approach cannot apply to hollow core samples, nor allow 3D experiments.

CN 2613754 Y discloses a tri-axial stressing rock core clamp holder, capable of preheating and maintaining temperature, with an inlet plug locking cap fixed on a radial pressurizing cylinder end, an outlet plug locking cap, a deforming compensation bar capable of axially sliding to compensate for deformation of a heat exchange coil, a fluid inlet joint pipe line, an axial pressurizing fluid pipe line, an axial pressurizing control valve, a radial pressurizing fluid pipe line, a radial pressurizing control valve, a heat exchanging coil coiled by the same material as the fluid inlet pipe line, an axial pressurizing hydraulic cylinder, a sealing ring, an axial pressuring plug, an axial pressurizing plug cap, a packing rock core rubber barrel, an electric heating device, a radial pressurizing tank, an outlet plug, a fluid outlet joint pipe line, and a temperature sensor. In this way, CN 2613754 Y provides a preheated and three axial stress loading core holder, which can be used for displacing experiments with a cylindrical core sample, but is used to conduct only one-dimensional experiments. CN 2613754 Y does not disclose hollow core samples, nor devices designed to test hollow core samples, nor three-dimensional displacing experiments related to the measurement of radial permeability.

U.S. Pat. No. 5,025,668 A describes a cell for triaxial stress testing of a rock sample, comprising a central body in which is placed a membrane enclosing the sample and exerting lateral stresses thereon, as well as a vertical pressurizer acting on a section of the sample. Its cell has means for measuring the deformation of the sample related to the applied stresses, whereby a membrane has a central lateral opening in which the sample is introduced, a lateral external surface coming into contact with the body of the cell, and a hollow internal volume forming a chamber providing confinement via a fluid introduced through an orifice. U.S. Pat. No. 5,025,668 A therefore discloses only a cell and testing method to measure the deformations of test rock sample related to study on rock mechanics and applicable to rock mechanics in geoscience. U.S. Pat. No. 5,025,668 A does not disclose application to a hollow core sample, nor measurement of liquid radial permeability of hollow core samples.

U.S. Pat. No. 5,226,310 A discloses methods and apparatuses for quantitatively measuring the strengths, pore pressures, and mechanical properties of low permeability geologic materials, such as shales, including a test specimen preparation apparatus for adjusting test specimen water content and test apparatus with an end cap having a pore pressure transducer channel disposed adjacent a test specimen filled with an immiscible, inert fluid which does not wet the test specimen, and controlling the deviatoric load on the test specimen during the test to prevent premature failure. U.S. Pat. No. 5,226,310 A can be used for the static test related to the rock mechanics in geoscience field, providing such results as the relationship between the axial stress and strains and the relationship of stress difference vs. strain with a variety of confining pressures. However, U.S. Pat. No. 5,226,310 A does not disclose a device or method for testing hollow core samples, nor 3D testing.

For evaluating the performance of chemical solution injection, such as polymer or gel solution injection, for oil recovery or conformance control, a filter cake often created by gel solutions can stick at the well wall, reducing the flow/penetration of foreign liquid injection. The present apparatus and method address the shortcomings of conventional testing devices and methods and more effectively screen potential chemical solution candidates for displacement efficiency, and permit more efficient evaluation of formation damage during drilling and acidic fluid processing.

Accordingly it is one object of the present disclosure to provide an apparatus and method to test geologic samples and determine different parameters such as liquid permeability, oil recovery factors by water, chemical solutions and supercritical $CO_2$, of reservoir rock samples, and evaluate formation damage caused by, for example, acidification and drilling process and performance of chemical solution for oil recovery study. The apparatus according to the invention may be used to determine the characteristics of shale rocks from formations containing hydrocarbons.

SUMMARY OF THE INVENTION

The present invention addresses one or more limitations or disadvantages of the art and provides physical property measurement capabilities for rock formations including sandstone, carbonate, limestone, and/or shale, as well as the capability to evaluate the degree of formation damage caused by, for example, fluid(s) injection and displacement efficiency, particularly in EOR and IOR processes. Aspects of the invention provide radial core flooding measurement apparatuses, systems, and methods useful for radial core flooding experiments, separately from or in addition to axial core flooding experiments, at evaluated temperature and/or pressure. Unlike conventional methods, in addition to external surface sample analysis, the invention may allow analysis of flow and/or pressure within hollow sample(s). Aspects of the invention allow injecting test fluid from the center hole of core sample into the hollow core sample, thus producing effluence from the outside surface of hollow core sample. The invention may further allows test fluid to be injected from the outside surface of hollow core sample into core sample and then produced effluence from the center hole of hollow core sample.

Aspects of the invention provide radial core-flooding apparatuses, comprising: a main body including a cylindrical cavity with a first end and a second end separated by a side wall along a longitudinal axis of the main body, the main body being configured to contain a subterranean core sample having an at least partially hollow central, axial cross-section; a disc-shaped flange, arranged within or upon the cylindrical cavity and releasably attached to the first end; a piston, arranged within the cylindrical cavity and removably and slidably disposed in a compartment of the second end, the piston being configured to hold the subterranean core sample; a flexible core sleeve, arranged within the cylindrical cavity and sealingly attached to the disc-shaped flange, the flexible core sleeve being configured to confine the subterranean core sample; an opening on the side wall suitable for injecting a confining fluid to the cylindrical cavity, the confining fluid being suitable to apply a circumferential stress to the flexible core sleeve and the subterranean core sample; an injection port arranged in the first end and the disc-shaped flange, injection port being configured to deliver an injection fluid to the at least partially hollow center of the subterranean core sample; a production port arranged in the first end and the disc-shaped flange, the production port being configured to collect a discharge fluid from the subterranean core sample; and an aperture on the second end suitable for injecting an overburden fluid to the compartment, the overburden fluid being configured to apply an axial stress to the subterranean core sample.

The injection port may include a sensor configured to detect pressure in the at least partially hollow center of the subterranean core sample.

The injection port may be configured to deliver at least 20% of a stream of the injection fluid into the at least partially hollow center of the subterranean core sample.

Inventive apparatuses may comprise more than one of the opening on the side wall and/or more than one of the aperture on the second end and/or a plurality of the production ports, wherein the production ports are symmetrically distributed about the circumference of the first end.

Inventive apparatuses may further comprise a first o-ring arranged sealingly between the disc-shaped flange and the main body; and/or a second o-ring arranged sealingly between the first end and the main body; and/or a third o-ring arranged sealingly between the second end and the main body; and/or a fourth o-ring arranged sealingly between the first end and the main body; and/or a fifth o-ring arranged sealingly between the first end and the main body.

The flexible core sleeve may comprise an elastomer in at least 50 wt. % of a sleeve total weight, which elastomer may be a fluoroelastomer present in an amount of at least 75 wt. % of the sleeve total weight.

The fluoroelastomer may comprise, in copolymerized form, hexafluoropropylene (HFP), vinylidene fluoride (VDF or VF2), tetrafluoroethylene (TFE), perfluoromethylvinylether (PMVE), or a mixture of three or more of any of these. The fluoroelastomer may have a fluorine content in a range of from 60 to 75 wt. %.

Inventive apparatuses may further comprise: a porous jacket having an annular, cylindrical shape with an outer side surface, an inside surface, a top surface, and a bottom surface, wherein the inside surface contacts the subterranean core sample, and wherein the porous jacket comprises a fluoropolymer in an amount of at least 50 wt. % of its total weight.

The fluoropolymer may comprise polytetrafluoroethylene (PTFE), perfluoroalkoxy alkane (PFA), fluorinated ethylene propylene (FEP), ethylene tetrafluoroethylene (ETFE), polyvinylidene fluoride (PVDF), polyvinylfluoride (PVF), ethylene chlorotrifluoroethylene (ECTFE), perfluoropropylvinylether (PPVE), perfluoromethylvinylether (PMVE), polychlorotrifluoroethylene (PCTFE), or a mixture of two or more of any of these. The fluoropolymer may have a density in a range of from 2 to 3.5 g/cm3, and/or a melting point in a range of from 215° to 375° C.

The main body may be configured to contain two or more subterranean core samples.

Inventive radial core-flooding systems may comprise: any inventive radial core-flooding apparatus described herein; a subterranean core sample with an at least partially hollow interior, disposed in the cylindrical cavity and confined with the flexible core sleeve such that the hollow interior is aligned with the injection port and an annular space exists between the flexible core sleeve and an inner surface of the main body; a first pump configured to deliver an injection fluid to the injection port; a second pump configured to deliver an overburden fluid to the at least one aperture so as to apply an axial stress to the subterranean core sample; a third pump configured to deliver a confining fluid to the at least one opening so as to apply a circumferential stress to the flexible core sleeve and the subterranean core sample; a first transducer configured to measure a pressure of the injection fluid; a second transducer configured to measure a pressure of the discharge fluid; and a third transducer configured to measure a differential pressure of the injection fluid and the discharge fluid.

The subterranean core sample(s) may have a cylindrical geometry including a lateral surface, a top base surface, and a bottom base surface, wherein the lateral surface of the subterranean core sample is covered with a porous jacket, and wherein the top and the bottom base surfaces are covered with a coating material.

Inventive radial core-flooding systems may further comprise: a vacuum sealed furnace, the radial core-flooding apparatus being enclosed within the vacuum sealed furnace; and a backpressure regulator configured to adjust a backpressure in the subterranean core sample.

Inventive methods of measuring subterranean core sample permeability may use any inventive system described herein, and involve: delivering the overburden fluid to the at least one aperture; delivering the injection fluid to the injection port, while concurrently delivering the confining fluid to the at least one opening to apply a circumferential stress to the flexible core sleeve and the subterranean core sample, the injection fluid permeating through the subterranean core sample and a discharge fluid being collected from the production port; measuring a differential pressure of the injection fluid at the injection port and the discharge fluid at the production port; and measuring the permeability of the subterranean core sample using the Darcy equation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2b shows a cross-sectional view along the axial direction of the porous jacket of FIG. 2a;

FIG. 3b shows a cross-sectional view along the axial direction of the disc-shaped flange of FIG. 3a;

DETAILED DESCRIPTION OF THE PREFERRED EMBODIMENTS

Radial core flooding apparatuses within the scope of the invention may comprise one or more radial core holder(s), oven(s), injection pump(s), confining pressure pump(s), overburden pressure pump(s), transducer(s), backpressure regulator(s), fraction collector(s), manual valve(s), autovalve(s), cross connector(s), accumulator(s), and computer data acquisition system(s).

Aspects of the invention provide a radial core flooding system and radial core flooding apparatus for measuring rock (e.g., geologic sample such as earth) properties and degree(s) of formation damage generated during various well-construction operations, as well as methods for using the same. The inventive devices and methods are likewise useful in evaluating performance and displacement efficiency of IOR and EOR processes based upon radial flow pattern(s).

Inventive radial core flooding apparatuses permit simulation and measurement of radial core flooding and physical displacement processes in oil and gas reservoirs at specific reservoir conditions (for example, temperature and pressure). The inventive radial flooding apparatuses may provide for the injection of a single or plural fluids into a hollow core sample. Dual radial core flooding apparatuses may provide for the simultaneous injection of separate fluids into two core plugs, simultaneous injection of a single fluid, or injections of fluid(s) separately concurrently or sequentially. The radial core flooding apparatuses of the present disclosure may provide for different injection direction into or through a hollow core sample, such as injection from a central cavity or from the outside of the hollow core sample towards its central axis. The radial core flooding apparatuses of the present disclosure can allow measurement of differential pressures across each tested hollow (at least partially) core in core flooding tests. The radial core flooding apparatus may further provide accurate and stable pore pressure assessments and measurement of each tested hollow core and accurate and stable confining pressure and overburden pressure in the radial core holder.

An aspect of the invention provides a radial core-flooding apparatus, comprising: a main body including a cylindrical cavity with a first end and a second end separated by a side wall along a longitudinal axis of the main body, the main body being configured to contain a core sample (e.g., a core sample composed of subterranean rock or earth) having an at least partially hollowed central, axial cross-section, or even an annular axial cross-section; a disc-shaped flange, arranged within the cylindrical cavity and releasably attached to the first end; a piston, arranged within the cylindrical cavity and removably and slidably disposed in a compartment of the second end, the core sample being configured to sit on the piston; a flexible core sleeve, arranged within the cylindrical cavity and sealingly attached to the disc-shaped flange, the flexible core sleeve being configured to confine the core sample; an opening, preferably a plurality of openings, on the side wall suitable for injecting a confining fluid to the cylindrical cavity, the confining fluid being suitable to apply a circumferential stress to the flexible core sleeve and the core sample; an injection port arranged in the first end and the disc-shaped flange, injection port being configured to deliver an injection fluid to the subterranean core sample and at least partially hollow center thereof; a production port arranged in the first end and the disc-shaped flange, the production port being configured to collect a discharge fluid from the subterranean core sample; and an aperture, preferably a plurality of apertures, on the second end suitable for injecting an overburden fluid to the compartment, the overburden fluid being configured to apply an axial stress to the subterranean core sample.

The above embodiments may include any combination of the following features.

The subterranean core sample (e.g., "core sample") preferably has an annular axial cross-section, i.e., cut in the direction orthogonal to the axial direction of the subterranean core sample, but may have an only partially hollowed central, axial cross-section, or a completely hollowed central space. The outer form of the subterranean core sample may be generally circular cylindrical, but the outer perimeter/circumference of cross-section of the subterranean core sample may be ovular, triangular, rectangular (such as square), rhomboidal, pentagonal, hexagonal, or amorphous. The shape of the outer perimeter of the subterranean core sample cross-section may be substantially that of an ideal shape, e.g., circle, but will normally deviate based on customary machining capabilities.

Given the at least partially hollowed shape of the subterranean core sample, the axial cross-section will have an inner perimeter corresponding to the hollowed-out space. The inner perimeter may be preferably an annular cross-section, but may alternatively be triangular, rectangular, or the like, and will generally deviate from the ideal geometry by machining capabilities. The annular axial cross-section has an inner radius, i.e., the radius from the center of the subterranean core sample to the inner perimeter, and an outer radius, i.e., the radius from the center of the subterranean core sample to the outer perimeter. A ratio of the inner radius to the outer radius of the annular axial cross-section may be in a range of from 2:1 to 1:1000, with the lower end of the ratio range optionally being 2:1, 1.5:1, 1:1, 1:1.5, 1:2, 1:2.5, or even 1:5, and the upper end of the ratio range optionally being 1:1000, 1:750, 1:500, 1:250, 1:100, 1:75, 1:60, 1:50, 1:45, 1:40, 1:35, 1:30, 1:25, 1:20, 1:15, 1:12.5, 1:10, 1:8, 1:7.5, 1:6.25, or even 1:5, 1:4, or 1:3.

The injection port(s) may further include a sensor configured to detect pressure in the at least partially hollow center of the subterranean core sample, whereby the injection port sensor may be integrally combined with a corresponding injection port(s), or separate from that injection port either within the same cavity or in a cavity of its own, relative to the corresponding injection port.

The injection port(s) may be configured to deliver at least 20%, 35%, 50%, 65%, 80%, or 95% of a stream of the injection fluid into the at least partially hollow center of the subterranean core sample.

Inventive apparatuses may preferably comprise more than one opening on the side wall, such as 2, 3, 4, 5, 6, 7, 8, 9, 10, 20, 36, 50, or more openings. The number of openings may be fewer than 1000, 640, 360, 180, 120, 80, 64, or fewer openings.

Inventive apparatuses may comprise one, or more than one, of the aperture on the second end, particularly 2, 3, 4, 5, 6, 7, 8, 9, or 10.

Inventive apparatuses may comprise a plurality of the production port, such as 2, 4, 6, 8, 10, 12, or any odd number in between. The plural production ports may be symmetrically distributed about the circumference of the first end, but are not required to be.

Inventive apparatuses may further comprise a first o-ring arranged sealingly between the disc-shaped flange and the main body; and/or a second o-ring arranged sealingly between the first end and the main body; and/or a third o-ring arranged sealingly between the second end and the main body; and/or a fourth o-ring arranged sealingly between the first end and the main body; and/or a fifth o-ring arranged sealingly between the first end and the main body. The material of which any of these o-rings are made will generally be resistant to high temperature and caustic environments, often having elastomeric properties. Exemplary materials for the o-ring(s) include natural rubber, synthetic polyisoprene, polybutadiene, polychloroprene, optionally halogenated butyl rubber (copolymer of isobutene and isoprene), styrene-butadiene rubber, optionally halogenated nitrile rubber (copolymer of butadiene and acrylonitrile), ethylene-propylene rubber (EPM), EPDM rubber (a terpolymer of ethylene, propylene, and a diene), epichlorohydrin rubber (ECO), acrylic rubber (ACM), silicone rubber, fluorosilicone rubber (FVMQ), fluoroelastomer (FKM), perfluoroelastomer (FFKM), polyether block amides (PEBA), chlorosulfonated polyethylene (CSM), ethylene-vinyl acetate (EVA), or a mixture of two or more of any of these, particularly fluoroelastomers and perfluoroelastomers. Preferable primary materials, i.e., highest component content of the total, for the o-rings may include vinylidene difluoride (VDF)-hexafluoropropylene (HFP) copolymer, ethylene-tetrafluoroethylene (TFE) copolymer, propylene-TFE copolymer, VDF-HFP-TFE terpolymer, ethylene-VDF-HFP-TFE terpolymer, ethylene-TFE-perfluoromethylvinylether (PMVE) terpolymer, whereby the fluorine content of the fluoroelastomer may be in the range of from 60 to 75%, or 65 to 70%, or 66%, 67%, 68%, 69%, or 70%.

The flexible core sleeve is flexible in the sense that the core sleeve is at least able to elastically respond to stress, and may comprise an elastomer, such as any of those described above for the o-ring(s), in at least 50, 60, 70, 75, 80, 85, 90, or 95% wt. % of a sleeve total weight. The core sleeve may be entirely made of elastomer, preferably only including fillers and/or additives useful for impart desired mechanical properties, such as impact strength. The elastomer of the core sleeve preferably may be a fluoroelastomer, and is present in an amount of at least 75, 85, 90, 92.5, 95, or 97.5 wt. % of the core sleeve total weight. The fluoroelastomer of the core sleeve may comprise, in copolymerized form, hexafluoropropylene (HFP), vinylidene fluoride (VDF or VF2), tetrafluoroethylene (TFE), perfluoromethylvinylether (PMVE), or a mixture of three or more of any of these. The fluoroelastomer of the core sleeve may have a fluorine content in a range of from 60 to 75, 65 to 70, or 66 to 70 wt. %. The fluoroelastomer of the core sleeve may preferably comprise VDF/HFP and/or VDF/HFP/TFE.

Inventive apparatuses may further comprise a porous jacket having an annular, cylindrical shape with an outer side surface, an inside surface, a top surface, and a bottom surface. The inside surface of the porous jacket may indirectly or, preferably, directly contact the subterranean core sample. The porous jacket may comprise a fluoropolymer in an amount of at least 50, 65, 80, 90, 95, or 97.5 wt. % of its total weight. The porous jacket may be entirely made of fluoropolymer, only including fillers and/or additives useful for impart desired mechanical properties, such as heat resistance, temperature resistance, coefficient of friction, etc. The fluoropolymer may preferably comprise polytetrafluoroethylene (PTFE), perfluoroalkoxy alkane (PFA), fluorinated ethylene-propylene (FEP), ethylene-tetrafluoroethylene (ETFE), polyvinylidene (di)fluoride (PVDF), polyvinylfluoride (PVF), ethylene chlorotrifluoroethylene (ECTFE), perfluoropropylvinylether (PPVE), perfluoromethylvinylether (PMVE), polychlorotrifluoroethylene (PCTFE), or a mixture of two or more of any of these, particularly PTFE. The fluoropolymer may have a density in a range of from 2 to 3.5, 2.1 to 3.0, 2.15 to 2.75, or 2.175 to 2.5 g/cm$^3$, not accounting for the porosity discussed below. The fluoropolymer may have a melting point in a range of from 215° to 375° C., 265 to 350° C., 300 to 330° C.

The porosity of the jacket will generally be at least 18% void volume at specific gravities of around 2.0, particularly a porosity in a range of from 20 to 75 vol. %, based on the total volume of the porous jacket, particularly 30 to 70 vol. %, 40 to 65 vol. %, 45 to 60 vol. %, or above 50 vol. %. Porosity end points in ranges acceptable for porous jacket within the invention are at least 20 vol. %, 25 vol. %, 30 vol. %, 35 vol. %, 40 vol. %, or 45 vol. %, and at most 80 vol. %, 72.5 vol. %, 67.5 vol %, or 62.5 vol. %. PTFE useful in the invention may have a specific gravity in a range of from 0.8 to 1.8, or 1.00 to 1.54, or 1.15 to 1.41, compared to pure non-porous PTFE typically having a specific gravity of 2.16. Pore sizes of the jacket material may be in the range of from 0.01 μm to 1 mm, 0.1 to 500 μm, 0.5 to 250 μm, 1 to 125 μm, or 2 to 50 μm. Pore sizes end points in ranges acceptable for porous jacket within the invention are at least 0.1 μm, 1 μm, 2.5 μm, 5 μm, 7.5 μm, 10 μm, 25 μm, 50 μm, or 100 μm, and at most 1 mm, 800 μm, 750 μm, 700 μm, 625 μm, 550 μm, 450 μm, 325 μm, or 275 μm. The thickness of the porous jacket sheet may be in a range of from 100 μm to 20 mm, 250 μm to 10 mm, 0.5 to 7.5 mm, or 0.75 to 5 mm.

The main body may be configured to contain two or more subterranean core samples, e.g., two samples in series, or four samples in parallel, etc., though the preferred implementation is presently believed to use a single subterranean core sample.

Radial core-flooding systems within the scope of the invention may comprise any inventive radial core-flooding apparatus described herein; a subterranean core sample with an at least partially hollow interior (generally having an annular axial cross-section, i.e., donut-shape along the height, of the cylindrical sample), disposed in the cylindrical cavity and confined with the flexible core sleeve (such as one described above, particularly one comprising fluoroelastomer, such as a VITON™ fluoroelastomer), such that the hollow interior is aligned with the injection port and an annular space exists between the flexible core sleeve and an inner surface of the main body; a first pump configured to deliver an injection fluid to the injection port; a second pump configured to deliver an overburden fluid to the at least one aperture so as to apply an axial stress to the subterranean core sample; a third pump configured to deliver a confining fluid to the at least one opening so as to apply a circumferential stress to the flexible core sleeve and the subterranean core sample; a first transducer configured to measure a pressure of the injection fluid; a second transducer configured to measure a pressure of the discharge fluid; and a third transducer configured to measure a differential pressure of the injection fluid and the discharge fluid. The first and second transducers may also function dually, such that outward radial pressure—outwardly from the center of the cylindrical sample, as well as inward radial pressure—inwardly from the outer perimeter of the cylindrical sample towards the center, may be measured concurrently. The transducers may also function to monodirectionally measure, whereby the transducers may be supplemented to measure with two (or more) monodirectional arrangements covering both inward and outward radial pressure. Moreover, inventive systems may be arranged with multiple sensors such that averages and other statistical values may be obtained from a "single" measurement.

Figure 2A:
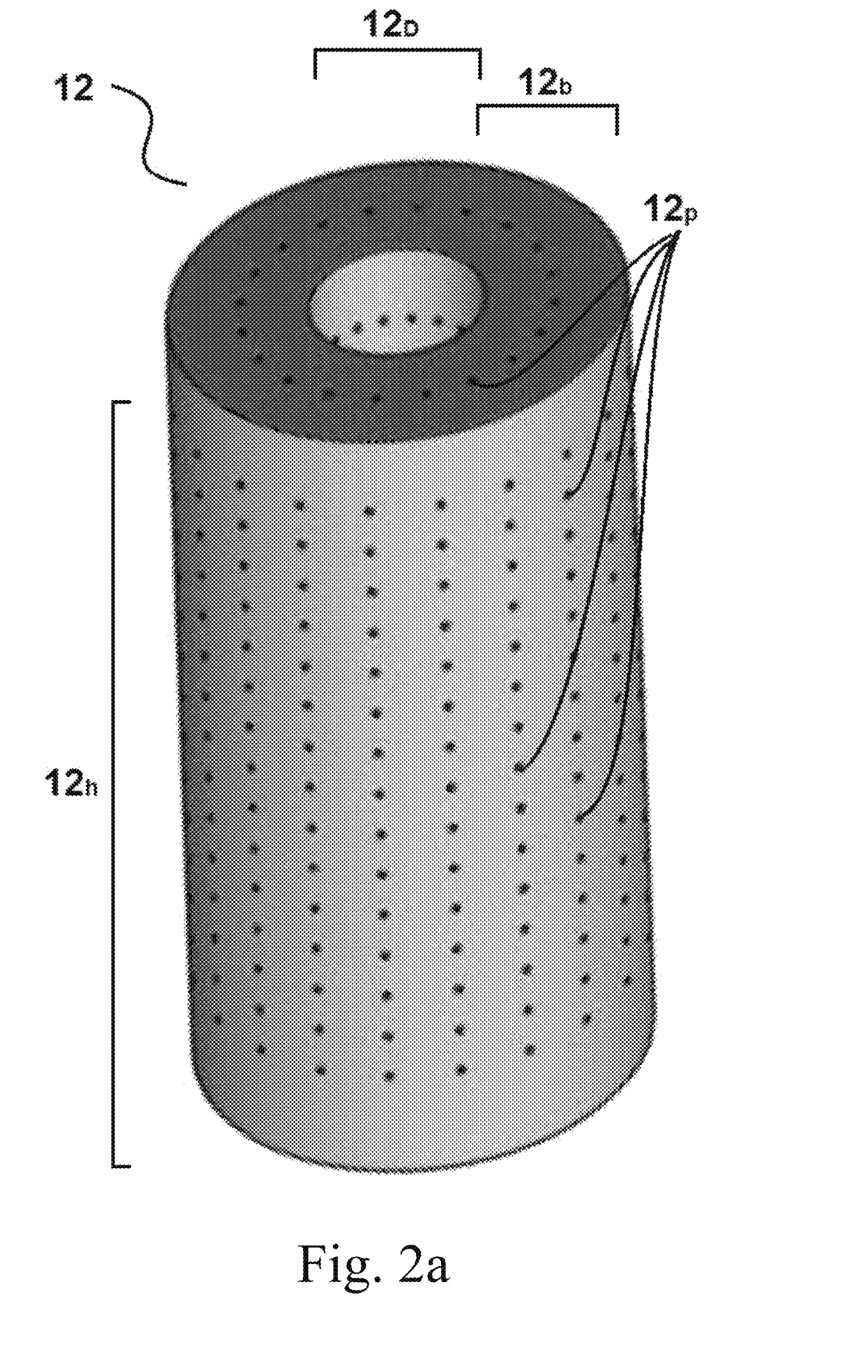
FIG. 2a shows a top perspective view of an exemplary porous jacket for fluid injection or production within the scope of the invention.
Figure 2B:
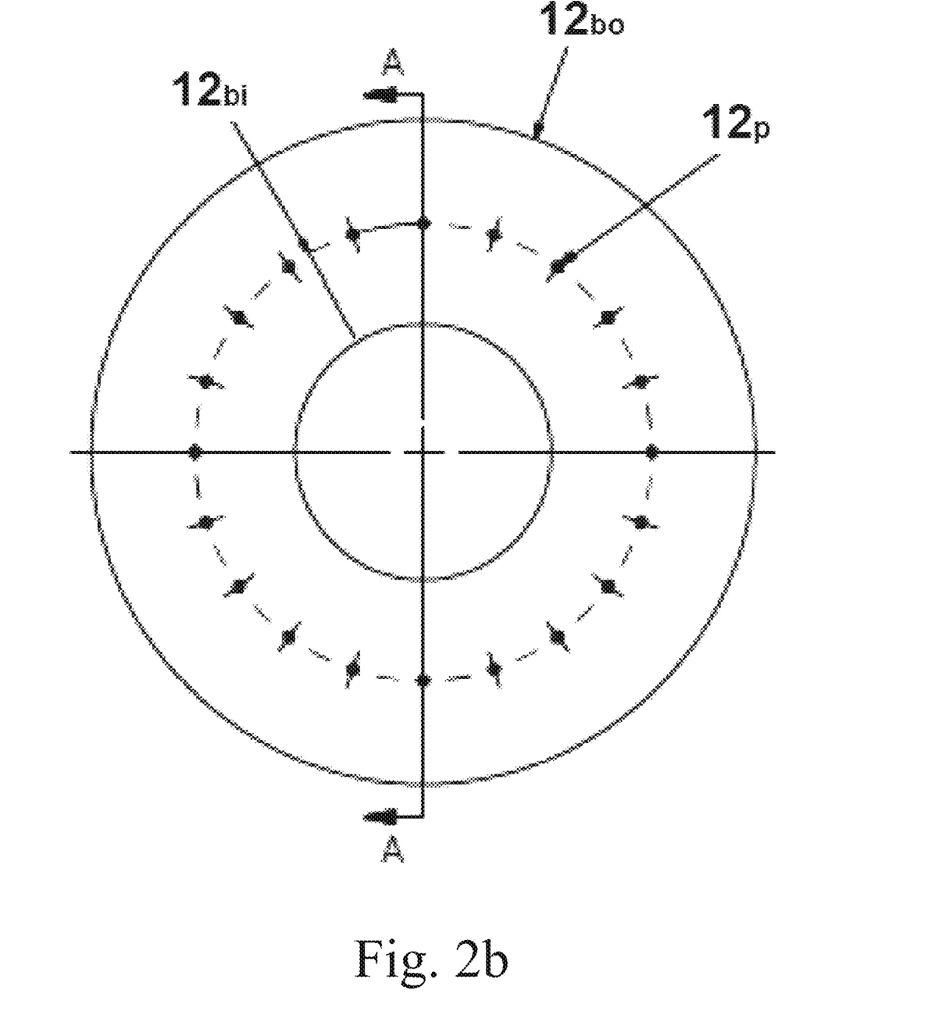
Figure 2C:
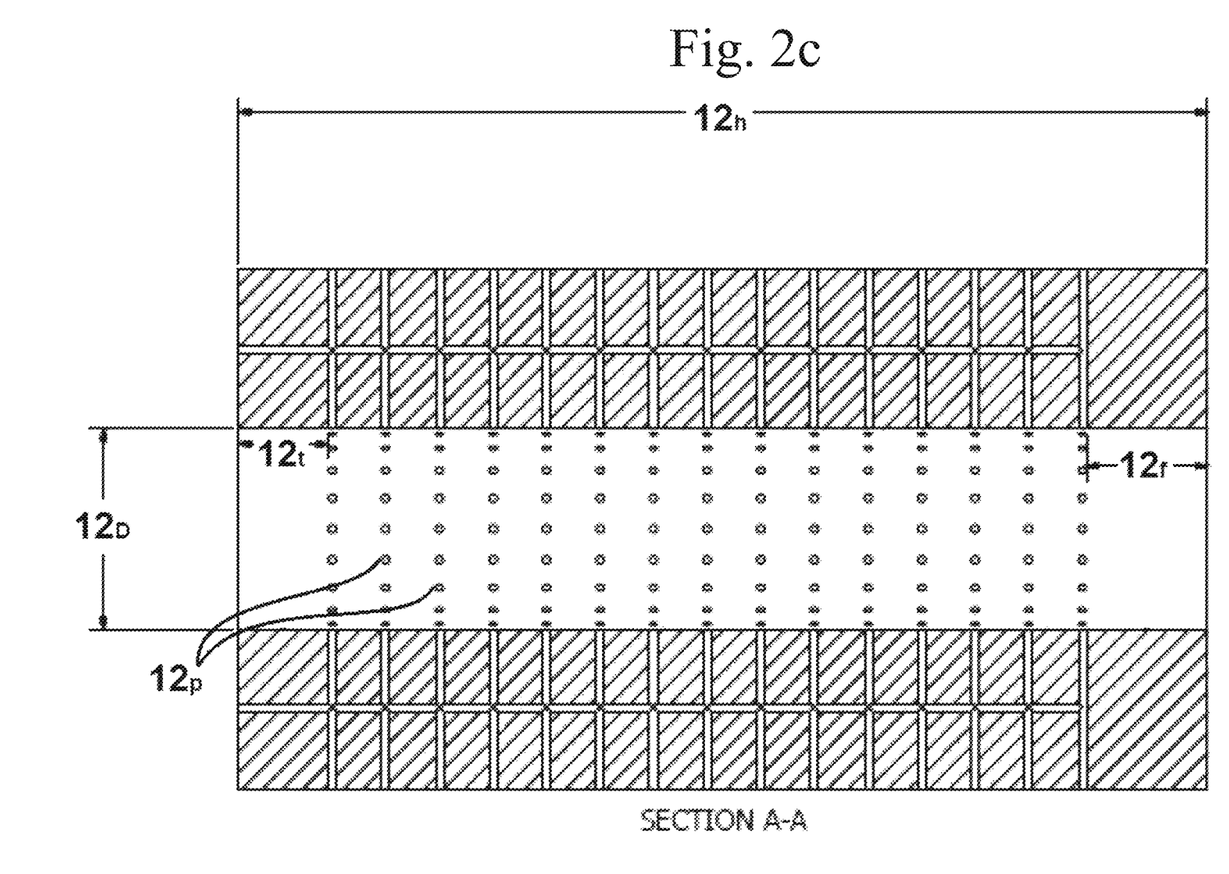
FIG. 2c shows an elevational cross-sectional view of the porous jacket of FIG. 2a, along the line A-A as shown in FIG. 2b.

The subterranean core sample in the system or apparatus may preferably have a cylindrical geometry including a lateral surface (along its outer perimeter, i.e., a rectangle wrapped around circular ends), a top base surface, and a bottom base surface, wherein the lateral surface of the subterranean core sample is covered with the porous jacket as described above and an embodiment of which is exemplified in FIG. 2. Separately, or together with the preceding, the top and the bottom base surfaces may be covered with a coating material. The top and bottom base surfaces may be generally planar, in line with machining limitations, and overlooking the hollowing towards their centers, though the top base surface and/or bottom base surface must not be planar, and may be rough or textured. The coating may be transient, such as an oil or grease coating, or semi-permanent, i.e., intended to remain in place for several uses, such as a fluoropolymer material as described herein.

Inventive systems may further comprise a vacuum sealed furnace configured to enclose the radial core-flooding apparatus entirely within the vacuum sealed furnace. Inventive systems may further comprise a backpressure regulator configured to adjust a backpressure in the subterranean core sample.

Inventive methods involve measuring the permeability of the subterranean core sample, e.g., with systems and apparatuses as described herein, wherein the method comprise delivering the overburden fluid to the at least one aperture; delivering the injection fluid to the injection port, while concurrently delivering the confining fluid to the at least one opening to apply a circumferential stress to the flexible core sleeve and the subterranean core sample, the injection fluid permeating through the subterranean core sample and a discharge fluid being collected from the production port; measuring a differential pressure of the injection fluid at the injection port and the discharge fluid at the production port; and measuring the permeability of the subterranean core sample using the Darcy equation.

The Darcy equation relates to, at constant elevation, a proportional relationship between the instantaneous discharge rate through a porous medium, the viscosity of the fluid and the pressure drop over a given distance:

$$Q = -\frac{\kappa A(p_b - p_a)}{\mu L}$$

The above equation for single phase (fluid) flow defines absolute permeability, specifically, single phase permeability, wherein the total discharge, Q (units of volume per time, e.g., m$^3$/s) is equal to the product of the intrinsic permeability of the medium, $\kappa$ (m$^2$), the cross-sectional area to flow, A (units of area, e.g., m$^2$), and the total pressure drop $p_b$-$p_a$ (pascals), all divided by the viscosity, $\mu$ (Pa·s) and the length over which the pressure drop is taking place, L (units of length, e.g., m).

Specific examples of useful fluoroelastomers within the scope of the invention include the "FKM" fluoroeslastomers (by ASTM D1418 standard, equivalent to FPM by ISO/DIN 1629 standard) and other fluorinated elastomers, such as perfluoro-elastomers (FFKM) and tetrafluoro ethylene/propylene rubbers (FEPM), and fluoroelastomers not containing vinylidene fluoride as a monomer, i.e., non-FKM fluoroelastomers. Useful FKM fluoroelastomers could include Type 1 FKMs, comprising vinylidene fluoride (VDF) and hexafluoropropylene (HFP) in polymerized form.

Alternate (or blendable with any other) useful FKM fluoroelastomers could include Type 2 FKMs, comprising VDF, HFP, and tetrafluoroethylene (TFE). Terpolymers of this sort have a higher fluorine content compared to copolymers (typically between 68 and 69 wt. % fluorine relative to about 66 wt. % for copolymers). Type 2 FKMs may have better chemical resistance and heat resistance at the cost of compression set and low temperature flexibility.

Further alternate (or blendable with any other) useful FKM fluoroelastomers could include Type 3 FKMs, comprising VDF, TFE, and perfluoromethylvinylether (PMVE). Type 3 FKMs may offer better low temperature flexibility relative to copolymers and Type 2 terpolymers. Type 3 FKMs generally have fluorine content ranges from 62 to 68 wt. %.

Still further alternate (or blendable with any other) useful FKM fluoroelastomers could include Type 4 FKMs, comprising propylene, TFE, and VDF, which offer increased high pH resistance relative to other types of FKMs, at the cost of worsened swelling properties, especially in hydrocarbons (increased swelling and distortion). Type 4 FKMs generally have a fluorine content of about 67 wt. %, i.e., from 66.5 to 67.5 wt. % or closer to 67 wt. %.

Further alternate (or blendable with any other) FKM fluoroelastomers could include Type 5 FKMs, comprising VDF, HFP, TFE, PMVE, and ethylene. Type 5 FKM has good high pH resistance (resistance to bases) and good high temperature hydrogen sulfide resistance, making them particularly attractive for use in the boring and bore analysis applications, as in the case of the present invention.

Commercially available fluoroelastomers from the Chemours Company are marketed under the trademark VITON™ fluoroelastomers with advanced polymer architecture (APA), VITON™ EXTREME™ fluoroelastomers, or VITON™ FREEFLOW™ fluoroelastomers, such as the VITON™ GLT-200S fluoroelastomer; VITON™ EXTREME™ ETP-600S fluoroelastomer, VITON™ GBL-200S fluoroelastomer, VITON™ GBL-600S fluoroelastomer, VITON™ GF-200S fluoroelastomer, VITON™ GF-600S fluoroelastomer, VITON™ GFLT-200S fluoroelastomer, VITON™ GFLT-600S fluoroelastomer, VITON™ GLT-600S fluoroelastomer, VITON™ A-100 fluoroelastomer, VITON™ A-200 fluoroelastomer, VITON™ A-331C fluoroelastomer, VITON™ A-361C fluoroelastomer, VITON™ A-401C fluoroelastomer, VITON™ A-500 fluoroelastomer, VITON™ A-601C fluoroelastomer, VITON™ A-700 fluoroelastomer, VITON™ AL-300 fluoroelastomer, VITON™ AL-600 fluoroelastomer, VITON™ B-202 fluoroelastomer, VITON™ B-600 fluoroelastomer, VITON™ F-605C fluoroelastomer, VITON™ B-303C fluoroelastomer, VITON™ VTR-9217 fluoroelastomer, which may be combined/blended to tailor properties to the desired application, e.g., based upon the VITON™ Chemical Resistance Guide, which is incorporated herein in its entirety.

The porous jacket which may surround and directly or indirectly contact the subterranean core sample in apparatuses, systems, and methods within the scope of the claim, will generally be made of a fluoropolymer as described herein (generally distinct from fluoroelastomers, though possibly including such fluoroelastomers in certain applications). Particularly preferred jackets comprise PTFE, which is commercially available under the mark TEFLON™ PTFE. Viton rubber sleeve, seal-set, Viton O-ring, fluid distribution end plug, supporting plug, jump ring, injection and production ports, pressure ports, confining fluid inlet and outlet ports, hydraulic piston and overburden fluid injection port.

Inventive radial core flooding apparatuses may include a radial core holder, oven, injection pump, confining pressure pump, overburden pressure pump, transducer, backpressure regulation (BPR), fraction collector, an N$_2$ cylinder/tank, auto-valve, and/or manual-valve, generally all of these and often in pluralities. Inventive radial core holders may be placed in an oven configured to control test temperature.

Core plug(s) or sample(s) suitable for use in the apparatuses, systems, and methods within the scope of the invention, may have a partially hollowed-out central region, up to a completely hollow central cavity. The core sample to be analyzed generally has a seal set on the top and bottom and is inserted into a high permeable porous jacket that is placed into a flexible sleeve that may be made using elastomer(s) and especially fluoroelastomer(s), e.g., VITON™ fluoroelastomer(s). A fluid distribution end plug and hydraulic piston may be respectively inserted the top and bottom of an assembly containing the core sample(s), a permeable porous jacket, and a flexible sleeve. This assembly may be placed into the main body of core holder supported by supporting plugs on the top and bottom of core holder. The radial core may be sealed in by axial stress provided by one or more overburden pumps and circumferential stress provided by one or more confining pumps.

To evaluate the degree of formation damage at or near the wellbore, or near-wellbore, for example, test fluid may be injected into the at least partially hollowed-out radial core of the sample from a central cavity of the sample, and produced from a (PTFE) porous jacket. The difference in pressures measured between the injector port(s) and the production port(s) can be determined by transducers placed in inlet and outlet (production) ports. Permeability to the test fluid is calculated using the Darcy radial flow equation. The degree of formation damage is defined as the ratio of a standard permeability of test core sample/plug to the measured permeability of test fluid through the subterranean core sample at same test conditions.

Diameters of cylindrical subterranean core samples, e.g., 1" (2.54 cm), 1.5" (3.81 cm), and 4" (10.16 cm), may be placed or located appropriately within the main body enclosure by pressing with, or changing dimensions of, the fluid distribution end plug. The lengthwise placement of subterranean core samples may adjusted by the hydraulic piston and/or one or more spacers between the subterranean core sample and the fluid distribution end plug.

Figure 1:
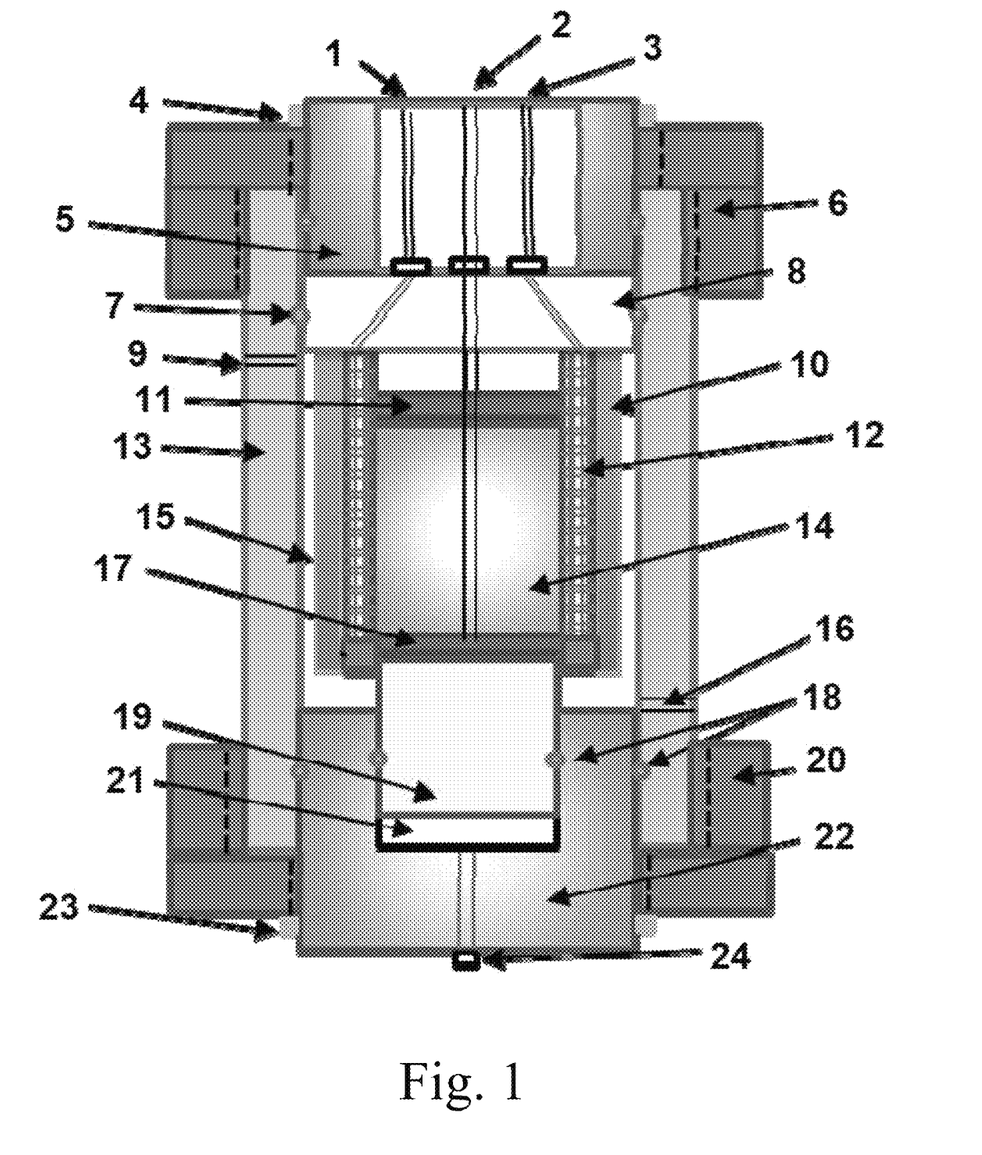
FIG. 1 shows a partial schematic cross-sectional view of a radial core-flooding apparatus for dynamic experiments within the scope of the invention.

Referring now to FIG. 1, which illustrates an exemplary radial core holder assembly, the subterranean core sample (14) with a central cavity, i.e., hollow core, is beset with a top seal-set (11) and a bottom seal-set (17). The core sample to be analyzed is inserted into a high permeable porous jacket (12), which is portrayed in an exemplary embodiment in FIG. 2, and the porous jacket (12) is placed into a flexible core sleeve (10), particularly one made of VITON™ fluoroelastomer(s). A fluid distribution end plug (8), of which an embodiment is excerpted and shown in FIG. 3, has three production port (1), one injection port (2), and three pressure measurement ports (3), and a hydraulic piston (19) are inserted the top and bottom of the assembly having core sample (14), surrounded by a highly permeable Teflon porous jacket (12), e.g., made primarily or entirely of PTFE, and a flexible core sleeve (10) made primarily or entirely of VITON™ fluoroelastomer(s). The assembly is placed into the main body (13) of core holder supported by supporting plugs (5) on the top and bottom (22) of core holder. The radial core plug (14) is sealingly held by axial stress provided by the overburden pump ($25_b$) connecting to injection port (2) for overburden fluid (24) and a circumferential stress providing by confining pump ($25_c$) connected to confining pressure port (16). The confining port (9) is used to release confining pressure.

Test fluid (injection fluid) is injected into core plug through an injection port (2) into the central cavity of the core sample (14). Injection pressure can be measured at injection port (2) as well. The pressure port (3), which may be placed radially outside of the core sample (14), can measure the outlet pressure. The effluent from the outside surface of core sample (14) may be collected in a fraction collector (27), as exemplified in FIG. 4, which may be connecting to the production port(s) (1). O-rings (7, 18), preferably made of VITON™ fluoroelastomer(s), can be respectively used to seal the main body (13) to prevent leakage of confining fluid (15) and to prevent leakage of overburden fluid (21). As seen exemplified in FIGS. 1 and 4, three connectors may used in the fluid distribution end-plug (8) to adjust the position of connection to the fraction collector (27) when the diameter of core sample (14) is varied during radial core flooding experiment(s). Supporting plug (5, 22), each being optionally sealed with o-rings, preferably from VITON™ fluoroelastomer(s), support a fluid distribution end-plug or disc-shaped flange (8) and hydraulic piston (19). The adjustment of the length of radial core plug (14) is achieved by hydraulic position (19) which is controlling by overburden pressure pump (24). The function of the jump rings (4, 23) exemplified in FIG. 1, is to hold the respective supporting plug (5, 22) in place. Glands (6, 20) may be used to connect main body (13) of radial core holder contained in the main body (13).

To evaluate the degree of formation damage in the near-wellbore, for example, test fluid may be injected into a cylindrical core sample (14) from the central cavity and produced from the porous jacket (12), e.g., a highly permeable Teflon porous media. Differential pressure between injection (2) and production port(s) (1) can be determined by transducer sensors (not shown) placed in injection (2) and pressure port(s) (1). The permeability of the core sample (14) to test fluid is calculated using the Darcy radial flow equation or any other suitable model. The degree of formation damage to test fluid is defined as the ratio of test fluid permeability of the subterranean core sample (14) to a standard permeability for the same subterranean core sample (14) under the same test conditions.

Figure 4:
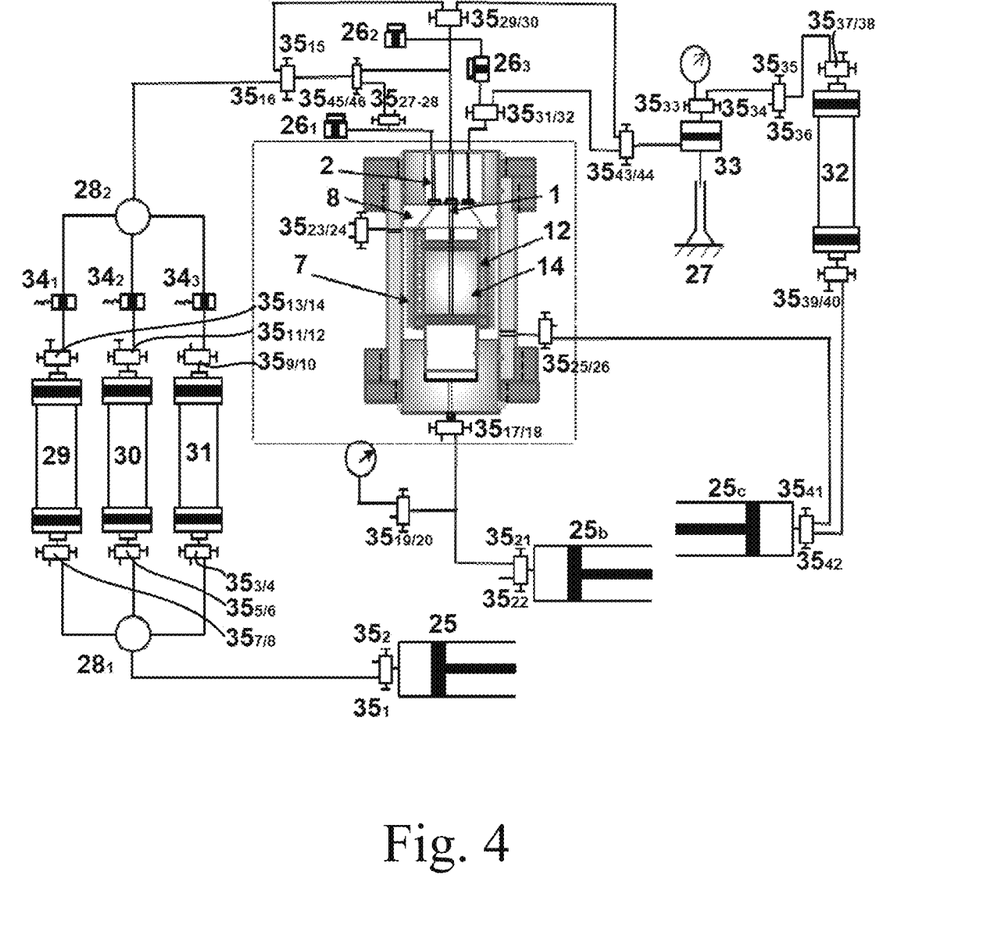
FIG. 4 shows a schematic diagram of a radial core flooding system suitable for testing dynamic properties of reservoir rock within the scope of the invention.

FIG. 4 illustrates an exemplary embodiment of an inventive system, wherein, generally, radial core flooding apparatuses are installed with a vertical orientation in an oven, allowing for the injection of test fluid(s) from either or both of within a central cavity of the core sample (14) and from a highly permeable porous jacket (12), preferably made using a fluoropolymer, particularly PTFE. The porous jacket (12) may directly contact an outside surface of the at least partially hollow core sample (14). The test fluid(s) may implement a variety of injection flow rates in the range of from 0.0001 to 400 cm³/min., 0.0005 to 200 cm³/min., 0.01 to 150 cm³/min., 0.5 to 125 cm³/min., 1 to 100 cm³/min., 2.5 to 75 cm³/min., 5 to 50 cm³/min., or 10 to 25 cm³/min., using one or more pumps (25).

Injection pump(s) (25) may connect to three piston accumulators (29, 30, 31) loaded with differential fluids through cross connector ($28_1$). Inlet injection pressure may be measured using a transducer ($26_2$). Accurate and stable confining and overburden pressure are respectively controlled by overburden pump(s) ($25_b$) and confining pump(s) ($25_c$). The confining pressure may be up to 10,000 psi (689.5 bar, 68.95 MPa) and the overburden pressure may be up to 6000 psi (413.7 bar, 41.37 MPa), depending on the type of rock. For example, the confining pressure may be in a range of from 30 to 9,000 psi (2.07 to 620.5 bar), 50 to 8,000 psi (3.45 to 551.6 bar), 100 to 7,500 psi (6.89 to 517.1 bar), 250 to 6,250 psi (17.2 to 430.9), or 500 to 5,000 psi (34.5 to 344.7 bar). The overburden pressure may be in a range of from 20 to 5,750 psi (1.37 to 396.4 bar), 40 to 5,500 psi (2.76 to 379.2 bar), 60 to 5,000 psi (4.14 to 344.7 bar), 75 to 4,500 psi (5.17 to 310.3 bar), or 100 to 4,000 psi (6.89 to 275.8 bar).

The production of oil and water can be separated and measured using the fraction collector (27) at ambient conditions. Three piston accumulators (29, 30, 31) may be located at the outside of the oven and can load differential fluids, such as brine, dead crude oil, live crude oil, supercritical $CO_2$, and chemical solutions. A pressure measurement system may include an upstream pressure transducer ($26_1$), downstream pressure transducer ($26_3$), and differential pressure transducer ($26_2$). These transducers ($26_1$, $26_2$, $26_3$) are mounted the outside of the oven (not shown) and the main body (13). Differential pressure(s) across a hollow core sample may be measured by upstream ($26_1$) and downstream ($26_3$) pressure transducers while running core flooding experiments.

Referring to FIG. 2a-c, which depict an exemplary porous jacket (12), preferably made with PTFE, the pores (12a) are distributed about the porous jacket (12). The porous jacket (12) exemplified in FIG. 2a-c is generally covered with pores ($12_p$) which may be symmetrically or asymmetrically arranged on the surface of the porous jacket (12). This porous jacket (12) has an interior diameter ($12_D$), generally in the range of from 1 to 3 in. (2.54 to 7.62 cm), 1.25 to 2 in (3.18 to 5.08 cm), or 1.4 to 1.7 in (3.56 to 4.32 cm), and an annular thickness ($12_b$), which may be in a range of from 0.75 to 4 in (1.91 to 10.2 cm), 1.5 to 3.5 in (3.81 to 8.89), 2.25 to 2.6 in (5.72 to 6.60 cm), defined by an interior radius ($12_{bi}$) and an outer radius ($12_{bo}$) from the center of the core sample (14), as well as a height ($12_h$), including heights in a range of from 4 to 15 in (10.2 to 38.1 cm), 5 to 12 in (12.7 to 30.5 cm), 6 to 9 in (15.2 to 22.9 cm), or 6.5 to 8 in (16.5 to 20.3 cm). The pores ($12_p$) may be optionally arranged a certain displacement from along the porous jacket height ($12_h$) from its top ($12_t$) and from its base ($12_f$), each of which may separately or identically be within 2 in (5.08 cm), 1.5 in (3.81 cm), 1 in (2.54 cm), or 0.75 in (1.91 cm).

Various data acquisition and/or processing systems may be used to collect data, such as upstream and downstream pressure, injection flow rate, confining pressure, overburden pressure, temperature, and pore pressure. Such processing systems may be mainframes, personal computers, laptops, tablets, or any number of personal electronic devices with sufficient computing capacity.

Inventive fluid(s) delivery systems (FDS) may utilize, for example, a QUIZIX-Q6000-10K pump (25), piston accumulators (29, 30, 31) with working pressures up to at least 10,000 psi and capacity in a range of from 100 mL to 10 L, 500 mL to 5 L, 1 to 3 L, or 2 L, cross connectors ($28_1$, $28_2$), auto-valves (34), and manual valves (35), and deliver fluids to the at least partially hollow core sample (14) in the main body (13) during experiments as exemplified in FIG. 4. The injection pump (25) may be set a paired constant flow rate in the range of 0.0001 to 400 cm$^3$/min., 0.0005 to 200 cm$^3$/min., or any rate described above, and pressure in the range of from 0.01 to 10,000 psi, 0.1 to 8,000 psi (6.89 mbar to 551.6 bar), 2.5 to 7,500 psi (172.4 mbar to 517.1 bar), 30 to 6,500 psi (2.07 to 448.2 bar), 125 to 5,750 psi (8.62 to 396.4 bar), etc., for example, using the QUIZIX-Q6000-10K pump, during core flooding tests.

The fluids delivery system may deliver fluid to (at least partially) hollow core sample (14) in the radial core holder main body (14) using one pump (25) or more, and an arrangement of piston accumulators (29, 30, 31), connectors (28), and valves (34, 35). The fluids delivery system may deliver one fluid at a constant flow rate in the range of from 0.0005 cc/min to 200 cc/min, or any rate discussed herein or otherwise customary for such tests (also gradients), and at a working pressure in the range of 1 psi to 10,000 psi, or, likewise, any rate discussed herein or otherwise customary for such tests.

Fluid accumulators useful in practicing the invention may be piston accumulators (29, 30, 31) manufactured by Coretest Systems, Inc., of Morgan Hill, Calif., USA. In some embodiments, the fluid accumulators may each have a delivery volume of about 2 liters and a maximum working pressure of about 10,000 psi. Examples of pumps (25) useful in the invention may be any of the QUIZIX Q6000-10K pump series, manufactured by Chandler Engineering of Tulsa, Okla., USA. Useful pumps (25) may have a maximum working pressure of 10,000 psi and a flow rate range of 0.0005 mL/min. to 200 mL/min.

As mapped in FIG. 4 as an example within the scope of the invention, the inventive system may include an arrangement of valves (34, 35) and connectors (28) to facilitate selective delivery of fluid to the main body (13). The pump (25) may be connected to manual valve ($35_1$), cross connector ($28_1$) to the bottom manual valve ($35_4$, $35_6$, $35_8$) of three accumulators (29, 30, 31). Manual valves ($35_{10}$, $35_{12}$, $35_{14}$) located on the top of three accumulators (29, 30, 31) may be connected to auto-valves ($34_1$, $34_2$, $34_3$), respectively, cross-connector ($28_2$), manual valves ($35_{15}$, $35_{27}$), and the injection port (2). The exemplary arrangement of valves (34, 35) and cross connectors (28) is depicted in FIG. 4.

In some embodiments, the effluent produced from the central cavity flows through manual valves ($35_{30}$, $35_{43}$), and a back-pressure regulator (BPR, 33) to a fraction collector (27). The back-pressure regulator (33) may be used to control the pore pressure of the (hollow) core sample (14).

A nitrogen (N$_2$) source (32) may provide part or all of the backpressure to the (hollow) core sample (14).

Figure 3A:
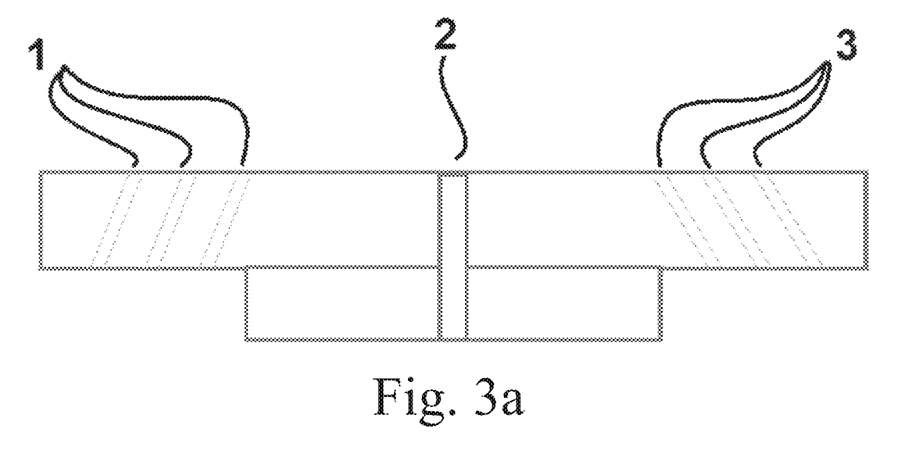
FIG. 3a shows an front elevational cross-sectional view of an exemplary fluid distribution end-plug (disc-shaped flange) within the scope of the invention.
Figure 3B:
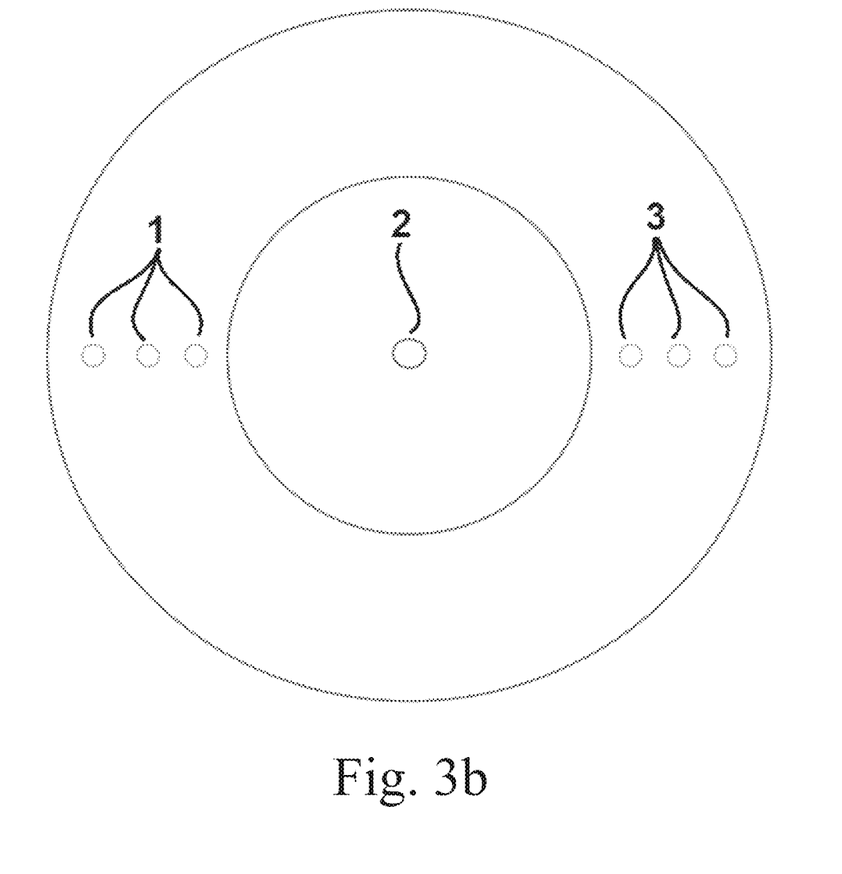

Inventive fluid distribution end plugs, or disc-shaped flanges (8) may be located at the top of seal set provides fluid distribution before injecting fluid into hollow core sample. There may be three injection parts (1, 2, 3) for example in the fluid distribution end plug (8), allowing adjustment of the translational displacement of the (hollow) core sample (14).

The N$_2$ in the back-pressure accumulator (32) may be pressurized by a confining pump ($25_c$) to provide an elevated backpressure for tests. Manual valve ($35_{42}$) may connect pump ($25_c$) through manual valve ($35_{40}$) at or near the base of the back-pressure (N$_2$) accumulator (32). Manual valves ($35_{35}$, $35_{37}$) may connect to manual valve ($35_{34}$) and brought into the BPR (33).

A transducer(s) (26), e.g., three or more, may be used to measure upstream pressure, downstream pressure, and differential pressure. Upstream pressure corresponds to injection pressure, and downstream pressure corresponds to production pressure. In some cases, production pressure may equal the pore pressure. As depicted in FIG. 4, transducers ($26_1$, $26_2$) may be used to measure the upstream pressure and downstream pressure when fluid is injected into a hollow core of a core sample (14) from the porous jacket (12). The differential pressure across the hollow core sample (14) may measured by transducer ($26_3$) when fluid is injected into hollow core of the sample (14) from the porous jacket (12).

The overburden pump ($25_b$) may provide overburden pressure to the bottom of the hollow core sample (14) as shown in FIG. 4. The overburden pump ($25_b$) may connect to manual valves ($35_{21}$, $35_{18}$) to a hydraulic piston (19) located at the base of the (hollow) core sample (14). The confining pump ($25_c$) may provide the confining pressure to the outside of hollow core sample (14) through a flexible core sleeve (10), preferably made using (VITON™) fluoroelastomer(s), and a porous jacket (12) via manual valves ($35_{41}$, $35_{26}$).

Figure 5:
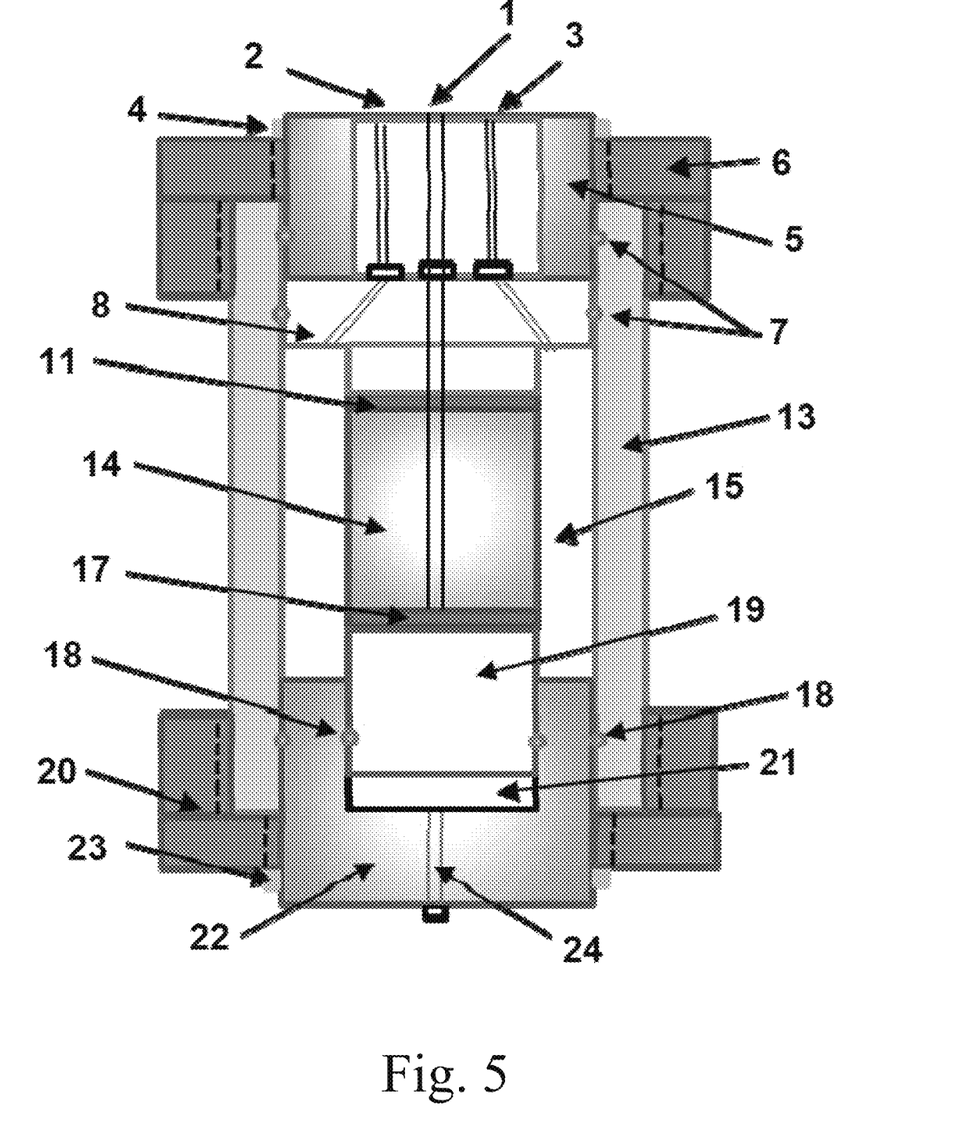
FIG. 5 shows a partial schematic cross-sectional view of a radial core-flooding apparatus for static experiments within the scope of the invention.
Figure 6:
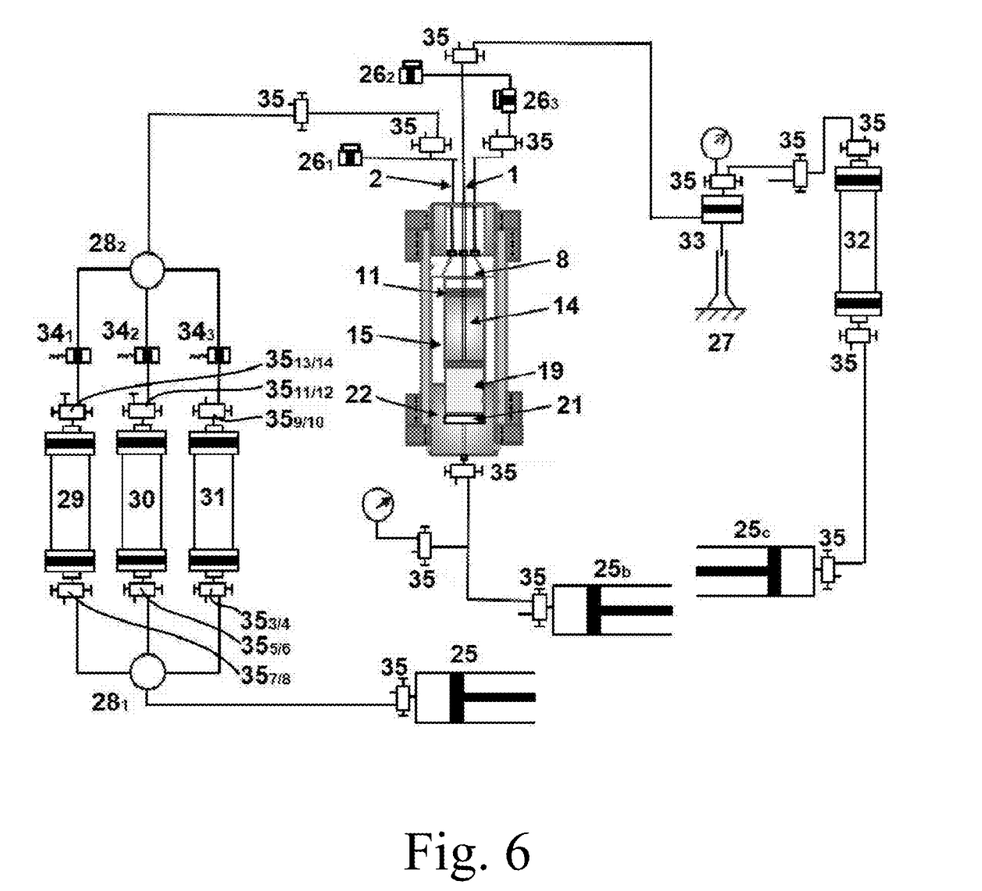
FIG. 6 shows a schematic diagram of a radial core flooding system suitable for testing static properties of reservoir rock within the scope of the invention.

In reference to FIGS. 5 and 6, which illustrate and example of an apparatus and system analyzing static properties of reservoir rock, a core sample (14) mounted seals on both ends may be placed in the main body (14), surrounded on the sides by confining fluid (15), optionally in lieu of the porous jacket (12) and flexible core sleeve (10). Overburden pressure, i.e., axial stress, may applied to the bottom of core sample (14) through a piston (19) using a pump (25). In this way, injection fluid (15) may fill annular space between the main body (13) of the apparatus and the core sample (14) and injected into the core sample (14) in the pattern of radial flow, which can produce effluent into and through a central hole of core sample (14). As in dynamic measurements, three transducers ($26_1$, $26_2$, $26_3$) may be provided to measure differential pressure between injection port(s) (2) and production port(s) (1), respectively constituting upstream and downstream pressure. The core sample (14), accumulators (29, 30, 31), oil-water separator (27), and auto-valves (34), may each be heated, e.g., with an oven. The injection flow rate is controlled by a pump (25) at a rate in the range of from 0.00025 to 80 cm$^3$/min, 0.001 to 75 cm$^3$/min, 0.005 to 70 cm$^3$/min, 0.01 to 60 cm$^3$/min, or 0.5 to 50 cm$^3$/min. A back pressure regulation system (33) may be used to control the pore pressure of the core sample (14). Injection fluid (15) outside the core sample(s) (14) may be injected into the core sample(s) (14) and flowing through and out of central hole (or at least partially hollowed central region in) of test core sample(s) (14). Data such as temperature, injection flow rate, upstream pressure, downstream pressure, differential pressure may be recorded by a data acquisition system.

Modifications and variations of the above-described embodiments in light of the above teachings and knowledge of persons of skill in the art are within the scope of the present invention. It is therefore to be understood that within the scope of the appended claims, the invention may be practiced otherwise than as specifically described herein.

REFERENCE SIGNS 1 production port
2 injection and pressure port
3 pressure port
4 (top) jump ring
5 (top) supporting plug
6 (top) gland
7 elastomeric o-ring(s)
8 distribution end plug/disc-shaped flange
9 (top) confining pressure opening
10 flexible core sleeve
11 (top) seal-set
12 porous jacket
$12_p$ pores
$12_D$ porous jacket interior diameter
$12_b$ porous jacket annular thickness
$12_h$ porous jacket height
$12_t$ pore displacement from top
$12_f$ pore displacement from base
13 main body
14 core sample
15 confining fluid
16 (bottom) confining pressure opening
17 (bottom) seal-set
18 elastomeric o-ring(s)
19 hydraulic piston
20 (bottom) gland
21 overburden fluid
22 (bottom) supporting plug
23 (bottom) jump ring
24 aperture for overburden fluid
25 pump(s); overburden pump (b); confining pump (c)
26 transducer(s)
27 fraction collector
28 cross connector
29 supercritical $CO_2$ accumulator
30 brine accumulator
31 dead/live oil accumulator
32 $N_2$ accumulator
33 back-pressure regulator
34 automatic valve
35 manual valve

The invention claimed is:

1. A radial core-flooding apparatus, comprising:
a main body including a cylindrical cavity with a first end and a second end separated by a side wall along a longitudinal axis of the main body, the main body being configured to contain a subterranean core sample having an at least partially hollow central, axial cross-section;
a disc-shaped flange, arranged within or upon the cylindrical cavity and releasably attached to the first end;
a piston, arranged within the cylindrical cavity and removably and slidably disposed in a compartment of the second end, the piston being configured to hold the subterranean core sample;
a flexible core sleeve, arranged within the cylindrical cavity and sealingly attached to the disc-shaped flange, the flexible core sleeve being configured to confine the subterranean core sample;
an opening on the side wall suitable for injecting a confining fluid to the cylindrical cavity, the confining fluid being suitable to apply a circumferential stress to the flexible core sleeve and the subterranean core sample;
an injection port arranged in the first end and the disc-shaped flange, the injection port being configured to deliver an injection fluid to the at least partially hollow center of the subterranean core sample;
a production port arranged in the first end and the disc-shaped flange, the production port being configured to collect a discharge fluid from the subterranean core sample; and
an aperture on the second end suitable for injecting an overburden fluid to the compartment, the overburden fluid being configured to apply an axial stress to the subterranean core sample.

2. The apparatus of claim 1, wherein the injection port includes a sensor configured to detect pressure in the at least partially hollow center of the subterranean core sample.

3. The apparatus of claim 1, wherein the injection port is configured to deliver at least 20% of a stream of the injection fluid into the at least partially hollow center of the subterranean core sample.

4. The apparatus of claim 1, comprising more than one of the opening on the side wall.

5. The apparatus of claim 1, comprising more than one of the aperture on the second end.

6. The apparatus of claim 1, comprising a plurality of the production ports, the production ports being symmetrically distributed about the circumference of the first end.

7. The apparatus of claim 1, further comprising:
a first o-ring arranged sealingly between the disc-shaped flange and the main body; and
a second o-ring arranged sealingly between the first end and the main body; and/or
a third o-ring arranged sealingly between the second end and the main body; and/or
a fourth o-ring arranged sealingly between the first end and the main body; and/or
a fifth o-ring arranged sealingly between the first end and the main body.

8. The apparatus of claim 1, wherein the flexible core sleeve comprises an elastomer in at least 50 wt. % of a sleeve total weight.

9. The apparatus of claim 8, wherein the elastomer is a fluoroelastomer, and is present in an amount of at least 75 wt. % of the sleeve total weight.

10. The apparatus of claim 9, wherein the fluoroelastomer comprises, in copolymerized form, hexafluoropropylene (HFP), vinylidene fluoride (VDF or VF2), tetrafluoroethylene (TFE), perfluoromethylvinylether (PMVE), or a mixture of three or more of any of these.

11. The apparatus of claim 9, wherein the fluoroelastomer has a fluorine content in a range of from 60 to 75 wt. %.

12. The apparatus of claim 1, further comprising:
a porous jacket having an annular, cylindrical shape with an outer side surface, an inside surface, a top surface, and a bottom surface,
wherein the inside surface contacts the subterranean core sample, and
wherein the porous jacket comprises a fluoropolymer in an amount of at least 50 wt. % of its total weight.

13. The apparatus of claim 12, wherein the fluoropolymer comprises polytetrafluoroethylene (PTFE), perfluoroalkoxy alkane (PFA), fluorinated ethylene propylene (FEP), ethylene tetrafluoroethylene (ETFE), polyvinylidene fluoride (PVDF), polyvinylfluoride (PVF), ethylene chlorotrifluoroethylene (ECTFE), perfluoropropylvinylether (PPVE), perfluoromethylvinylether (PMVE), polychlorotrifluoroethylene (PCTFE), or a mixture of two or more of any of these.

14. The apparatus of claim 12, wherein the fluoropolymer has a density in a range of from 2 to 3.5 g/cm$^3$.

15. The apparatus of claim 12, wherein the fluoropolymer has a melting point in a range of from 215° to 375° C.

16. The apparatus of claim 1, wherein the main body is configured to contain two or more subterranean core samples.

17. A radial core-flooding system, comprising:
the radial core-flooding apparatus of claim 1;
the subterranean core sample with the at least partially hollow interior, disposed in the cylindrical cavity and confined with the flexible core sleeve such that the hollow interior is aligned with the injection port and an annular space exists between the flexible core sleeve and an inner surface of the main body;
a first pump configured to deliver the injection fluid to the injection port;
a second pump configured to deliver the overburden fluid to the aperture so as to apply the axial stress to the subterranean core sample;
a third pump configured to deliver the confining fluid to the opening so as to apply the circumferential stress to the flexible core sleeve and the subterranean core sample;
a first transducer configured to measure a pressure of the injection fluid;
a second transducer configured to measure a pressure of the discharge fluid; and
a third transducer configured to measure a differential pressure of the injection fluid and the discharge fluid.

18. The system of claim 17, wherein the subterranean core sample has a cylindrical geometry including a lateral surface, a top base surface, and a bottom base surface,
wherein the lateral surface of the subterranean core sample is covered with a porous jacket, and
wherein the top and the bottom base surfaces are covered with a coating material.

19. The system of claim 17, further comprising:
a vacuum sealed furnace, the radial core-flooding apparatus being enclosed within the vacuum sealed furnace; and
a backpressure regulator configured to adjust a backpressure in the subterranean core sample.

20. A method of measuring a permeability of a subterranean core sample with the system of claim 17, the method comprising:
delivering the overburden fluid to the aperture;
delivering the injection fluid to the injection port, while concurrently delivering the confining fluid to the opening to apply the circumferential stress to the flexible core sleeve and the subterranean core sample, the injection fluid permeating through the subterranean core sample and the discharge fluid being collected from the production port;
measuring a differential pressure of the injection fluid at the injection port and the discharge fluid at the production port; and
measuring the permeability of the subterranean core sample using the Darcy equation.

* * * * *